(12) United States Patent
Renaux

(10) Patent No.: US 10,596,368 B2
(45) Date of Patent: Mar. 24, 2020

(54) QUADRIPOLAR IMPLANTABLE ELECTRODE FOR SEQUENTIAL NEUROSTIMULATION OF THE PHRENIC NERVE

(71) Applicant: SIRMED (EURL), Les Aires (FR)

(72) Inventor: Serge Renaux, Les Aires (FR)

(73) Assignee: ATROTECH, Tampere (FI)

( * ) Notice: Subject to any disclaimer, the term of this patent is extended or adjusted under 35 U.S.C. 154(b) by 113 days.

(21) Appl. No.: 15/735,853

(22) PCT Filed: May 17, 2017

(86) PCT No.: PCT/FR2017/000099
§ 371 (c)(1),
(2) Date: Dec. 12, 2017

(87) PCT Pub. No.: WO2017/203110
PCT Pub. Date: Nov. 30, 2017

(65) Prior Publication Data
US 2018/0161570 A1 Jun. 14, 2018

(30) Foreign Application Priority Data

May 25, 2016 (FR) ................................... 16 70261

(51) Int. Cl.
*A61N 1/05* (2006.01)
*A61N 1/36* (2006.01)

(52) U.S. Cl.
CPC ......... *A61N 1/0556* (2013.01); *A61N 1/0558* (2013.01); *A61N 1/3611* (2013.01)

(58) Field of Classification Search
None
See application file for complete search history.

(56) References Cited

U.S. PATENT DOCUMENTS

| | | |
|---|---|---|
| 4,940,065 A | 7/1990 | Tanagho et al. |
| 5,919,220 A | 7/1999 | Stieglitz et al. |
| 7,006,875 B1 * | 2/2006 | Kuzma ............... A61N 1/0553 600/372 |
| 2003/0040785 A1 | 2/2003 | Maschino et al. |

FOREIGN PATENT DOCUMENTS

WO 2017203110 A1 2/2003

OTHER PUBLICATIONS

Borgel Beatmunsmedizinische Diensleitungen and Technik, Brochure, Atrostim Phreniucus Nerven Stimulator, and English translation of p. 3.

* cited by examiner

*Primary Examiner* — Brian T Gedeon
(74) *Attorney, Agent, or Firm* — Patshegen IP LLC; Moshe Pinchas

(57) ABSTRACT

The invention relates to an implantable quadripolar electrode for sequential neurostimulation of the phrenic nerve. A matrix is provided with two branches each consisting of a hook designed to come in contact with the phrenic nerve without totally encircling it and an extension (112, 122), or strip, designed to cross the corresponding incision arranged in the pleura and fix the same on the pericardium, each hook having an orifice allowing the phrenic nerve to pass;
The hooks are connected with a bridge designed to keep them at a fixed distance from each other on the longitudinal plane of said phrenic nerve and to allow the rotation of the branches in relation to one another to position the hooks around the phrenic nerve via their respective openings.

12 Claims, 2 Drawing Sheets

QUADRIPOLAR IMPLANTABLE ELECTRODE FOR SEQUENTIAL NEUROSTIMULATION OF THE PHRENIC NERVE

CROSS-REFERENCE TO RELATED APPLICATION

This application is a 371 national stage application of International Application PCT/FR2017/000099, filed May 17, 2017, and claims the priority of French Application No. 1670261, filed on May 25, 2016.

FIELD OF THE INVENTION

The present invention relates to the field of multipolar implantable electrodes for multi sequential neurostimulation of the phrenic nerve needed to maintain artificial respiration and, more particularly, to those electrodes, quadripolar ones, that consist of two branches connected with a bridge that is designed to keep them at a well determined distance from each other on the longitudinal plane of the nerve with each being provided with two contactors arranged symmetrically around the axis of the said nerve and intended to be brought into contact therewith and to be powered with electric current for multi sequential neurostimulation via a bundle of cables.

It also relates to the operating method and the setting method.

TECHNOLOGICAL BACKGROUND

U.S. Pat. No. 4,940,065 describes an electrode adapted to be implanted surgically around a nerve bundle to provide selective: stimulation acting on certain parts of the nerve concerned.

The electrode comprises a biocompatible and dielectric carrier that starts from an open position and can be flattened to a closed position, completely encircling the nerve bundle, resulting in a constraint for postoperative inflammatory problems.

In its open position the carrier appears as a main body portion extending in the direction of a longitudinal winding axis of the carrier and flap portions extending transversely and outwardly from the opposite ends of the carrier. At least one electrode contact is fixed to an inner surface of the carrier and is welded to a conductive wire adapted for connection to a receptor implanted on the patient. As far as the method steps to manufacture the electrode are concerned, the carrier is originally a tube that is properly cut to form the main body and its flap portions. The contact of the electrode is then attached to an inner surface of the support and is welded to the conductor wire. It does not include a fixing device, i.e. the electrode can slide inducing the modification of the stimulation parameters.

ATROTECH company, acting under the trademark of "Atrostim", has designed an electrode which comprises two pairs of contactors arranged symmetrically around the nerve at a certain distance from one another on the longitudinal plane thereof.

During the stimulation sequence, which applies a combination of four electrical currents, the two opposite activated poles serve as cathode and anode and vice versa.

This results in the four combinations of stimulating actions generating low value electric currents.

This technology was developed to reduce the stressed nerve fatigue as it envisages activation of its only certain fibers allowing others to recover in the meantime.

The electrode in question includes a 1st branch that passes under the nerve and a 2nd that passes on it. The one that passes under the nerve comes out through a window created surgically under it; the matrix is held in place with sutures ensuring the contact with the nerve. On the other hand, the one that passes on the nerve is not maintained by it, and the contact of the contactors with the nerve is no longer assured. It is therefore necessary to use suture.

In addition the electrode in question is placed on each phrenic nerve (right and left) according to conventional invasive surgical practice (thoracotomy).

It therefore does not allow the use of trocar (no more than 10 mm in diameter) and, consequently, that of the video-controlled thoracoscopic technique, which is much less invasive.

SUMMARY OF THE INVENTION

The objective of the invention is to provide such an electrode that can be implanted by thoracoscopy, namely under video assistance, by means of a standard trocar, that would reduce the intervention time and the heavy postoperative consequences for the patient.

In the preferred embodiment of the invention the electrode is quadripolar.

In addition, the contact with the phrenic nerve of the two pairs of contactors is ensured by the shape of the branches, the positioning of the said contactors on the said branches and the elastic and flexible nature of the electrode.

The implantable quadrupole electrode for sequential neurostimulation of the phrenic nerve characteristically consists of a matrix provided with two branches, each consisting of a hook designed to come in contact with the phrenic nerve without totally encircling it and an extension, or tongue, designed to cross the corresponding incision arranged in the pleura and fix the same on the pericardium;

each hook has an aperture allowing the phrenic nerve to pass;

the said hooks are connected with a bridge designed to keep them at a fixed distance from each other on the longitudinal plane of said phrenic nerve and to allow, owing to its elasticity, the rotation of the branches in relation to one another to position the hooks around the phrenic nerve via their respective openings;

each of the said hooks is provided with two contactors arranged symmetrically around the axis of the said phrenic nerve, in contact with the same, that are meant to be powered with electrical current for multi-sequential neurostimulation via a bundle of four cables.

According to additional characteristics of the electrode as per the invention:

each extension, or tongue, comprises an orifice allowing for an easier fixing of each hook in contact with the phrenic nerve on the pericardium and the use of surgical clips;

the matrix is made of polytetrafluoroethylene;

the matrix is covered, on its face, which is not in contact with the nerve, with a silicone adhesive that can freeze the shape of the electrode while maintaining its optimum elasticity and flexibility to enable it to be put in place and its use.

Unlike U.S. Pat. No. 4,940,065 which describes an electrode:

as being adapted to be surgically implanted around a nerve bundle to ensure its selective stimulation acting on certain parts of the nerve concerned, this the electrode, according to the invention, is sequential and acts on the entire nerve;

as completely encircling the beam of the nerve causing a constraint resulting in a constraint for postoperative inflammatory problems, which is not the case of the electrode according to the invention;

as not having a fixing device, in other words the electrode can slide inducing the modification of the stimulation parameters, which is not the case of the electrode according to the invention;

For at least one of the aforementioned characteristics the electrode in U.S. Pat. No. 4,940,065 is not comparable to the present case relating to the phrenic nerve.

We are speaking about 2 non-transposable devices.

As a matter of fact the goals pursued, the technical solutions implemented and the results obtained are indeed totally different.

PRESENTATION OF FIGURES

The features and advantages of the invention will distinguish themselves more clearly while reading the detailed description, which follows, of at least one preferred embodiment thereof given by way of non-limiting example and shown in the accompanying drawings.

DETAILED DESCRIPTION OF THE INVENTION

Figure 1:
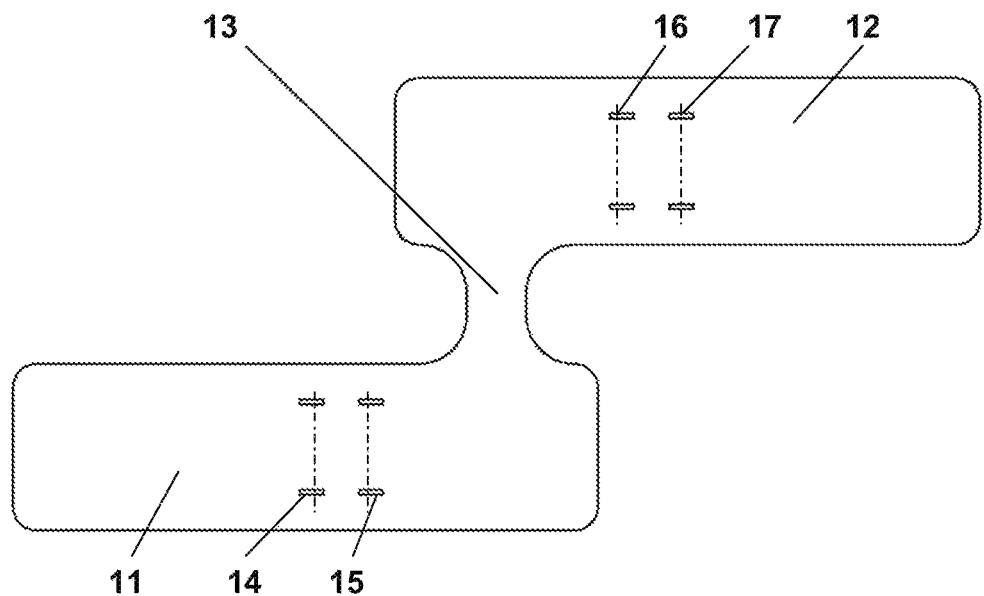
FIG. 1 represents, in developed view, the matrix of the electrode highlighting the contactor holding orifices.
Figure 2:
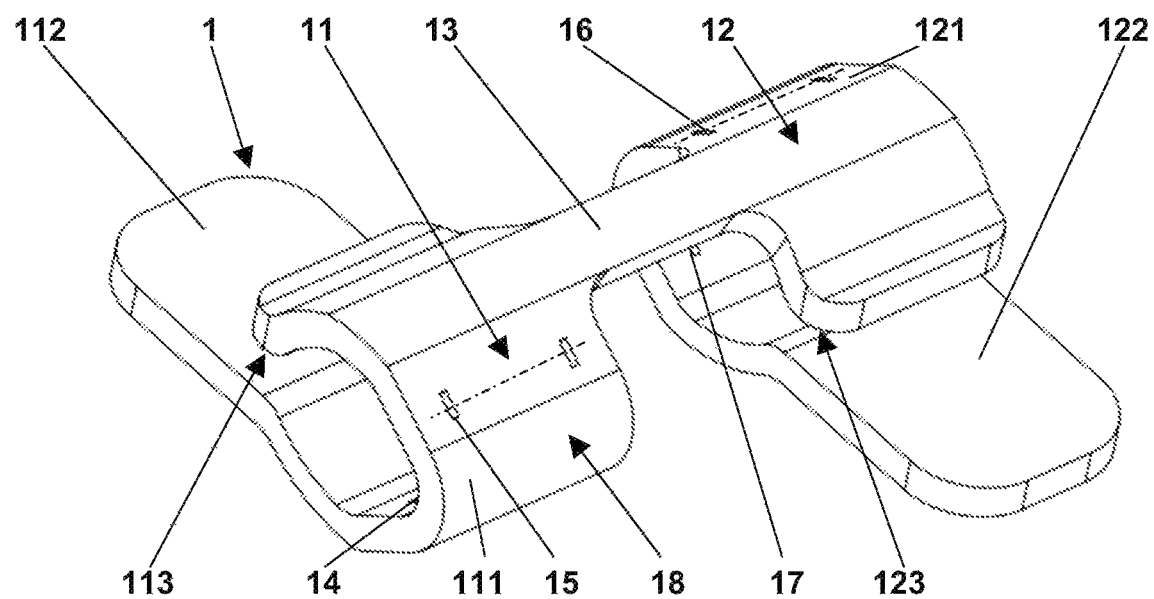
FIG. 2 represents, in 3D, the matrix of the electrode, according to FIG. 1.
Figure 3:
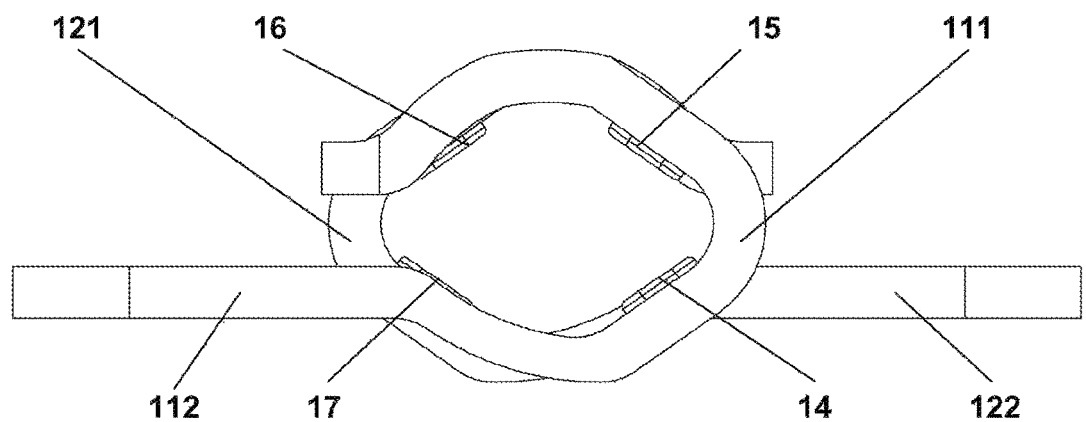
FIG. 3 represents, in profile view, the electrode with the position of the contactors highlighted.
Figure 4:
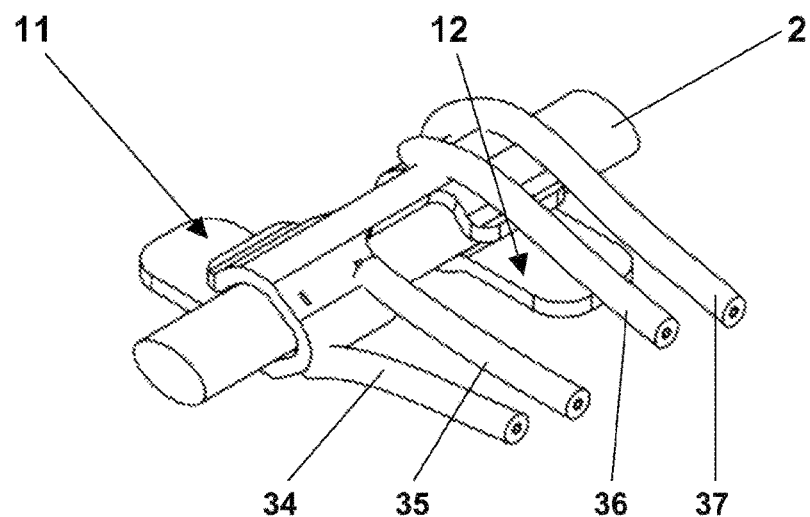
FIG. 4 represents, in 3D, the electrode with evidence of the position of the phrenic nerve and the power cables of the contactors.
Figure 5:
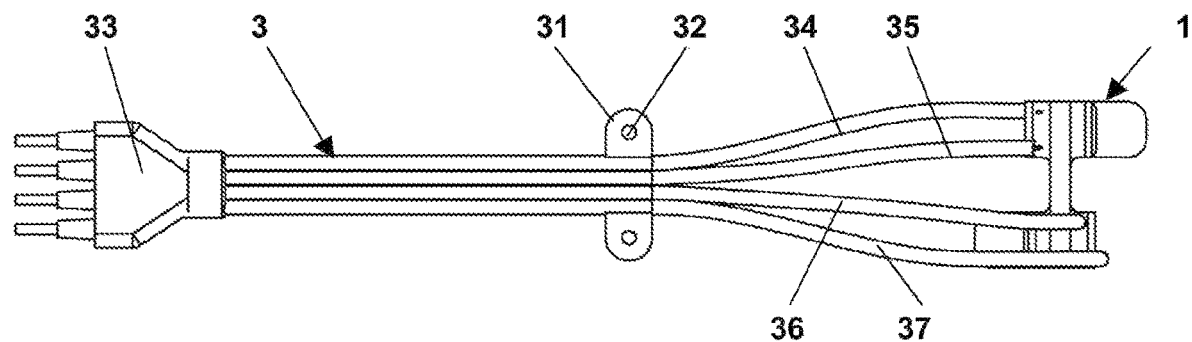
FIG. 5 represents, in elevation, the "electrode and wire harness" assembly.

The invention relates to an implantable quadripolar electrode (1) for multi sequential neurostimulation of the phrenic nerve (2).

According to the basic features of the invention as shown in the accompanying drawings:

the electrode consists of a matrix (1) provided with two branches (11) and (12), each consisting of a hook (111, 121) designed to come in contact with the phrenic nerve without totally encircling it and an extension (112, 122), or strip, designed to cross the corresponding incision arranged in the pleura and fix the same on the pericardium;

each hook (111, 121) has an aperture (113, 123) allowing the phrenic nerve to pass;

the hooks (111) and (121) are connected with a bridge (13) designed to keep them at a fixed distance from each other on the longitudinal plane of said phrenic nerve (2) and to allow, owing to its elasticity, the rotation of the branches (11) and (12) in relation to one another to position the hooks (111) and (121) around the phrenic nerve via their respective openings (113, 123);

the said hooks (111) and (121) are provided with two contactors (14, 15) and (16, 17) arranged symmetrically around the axis of the said phrenic nerve (2), in contact with the same, that are meant to be powered with electrical current for sequential neurostimulation via a bundle (3) of four cables (34, 35, 36, 37).

According to additional characteristics of the invention:

each extension (112, 122), or tongue, comprises an orifice (not represented) allowing for an easier fixing of each hook in contact with the phrenic nerve on the pericardium and the use of surgical clips;

the matrix (1) is made of polytetrafluoroethylene;

the contactors (14, 15, 16, 17), which are made of an electrically conductive material, are inserted into the walls of the matrix (1) during its manufacture.

the matrix (1) is covered, on its face (18), which is not in contact with the nerve (2), with a silicone adhesive that can freeze the shape of the electrode while maintaining its elasticity and flexibility to enable it to be put in place and its use;

the electric cables (34, 35, 36, 37) are held together by a device (31) with two orifices (32) designed to allow their attachment to the pleura, by suture, to avoid any risk of tension on the phrenic nerve (2).

The method of operation of the electrode as described above consists in supplying the contactors (14, 15, 16, 17), taken two by two, sequentially, in four phases, each contactor in turn being anode or cathode.

The electrode (1) and the connecting cables (3), according to the invention, are compatible with the implanted stimulator.

The ends of the cables (34, 35, 36, 37) that are opposite to the ends connected to the contactors (14, 15, 16, 17), are related to a plug (33) intended to be connected to the electrode's (1) power supply device.

Of course, those skilled in the art will be able to carry out the invention as described and represented by applying and adapting known means without the need to describe them or to represent them.

Other variants may also be resorted to without departing from the scope of the invention as determined by the content of the claims.

The invention claimed is:

1. An implantable quadrupole electrode (1) for sequential neurostimulation of a phrenic nerve (2), characterized in that the electrode consists of a matrix (1) provided with two branches (11) and (12), each consisting of a hook (111, 121) configured to be disposed adjacent a phrenic nerve and to come in contact with a phrenic nerve without totally encircling the phrenic nerve and an extension (112, 122), or strip, configured to cross the corresponding incision arranged in the pleura and configured to fix the electrode (1) on a pericardium;

in that each hook (111, 121) has an aperture (113, 123) configured to allow the phrenic nerve to pass therethrough;

in that the hooks (111) and (121) are connected with a bridge (13) configured to keep the hooks at a fixed distance from each other on the longitudinal plane of said phrenic nerve (2) and to allow, owing to its elasticity, the rotation of the branches (11) and (12) in relation to one another to position the hooks (111) and (121) around the phrenic nerve via their respective apertures (113, 123);

in that the said hooks (111) and (121) are provided with two contactors (14, 15) and (16, 17) are configured to be disposed symmetrically around the axis of the said phrenic nerve (2), in contact with the phrenic nerve, that are meant to be powered with electrical current for sequential neurostimulation via a bundle (3) of four cables (34, 35, 36, 37).

2. An implantable quadrupole electrode according to claim 1, characterized in that each extension (112, 122), or strip, comprises an orifice configured for an easier fixing of each hook on a pericardium and the use of surgical clips.

3. An implantable quadrupole electrode according to claim 1, characterized in that the matrix (1) is made of polytetrafluoroethylene.

4. An implantable quadrupole electrode according to claim 1, characterized in that the contactors (14, 15, 16, 17), which are made of an electrically conductive material, are inserted into the walls of the matrix (1) during its manufacture.

5. An implantable quadrupole electrode, according to claim 1, characterized in that the matrix (1) is covered, on its face (18), which is not in contact with the nerve (2), with a silicone adhesive that can freeze the shape of the electrode while maintaining its elasticity and flexibility.

6. An implantable quadrupole electrode, according to claim 1, characterized in that the electric cables (34, 35, 36, 37) are held together by a device (31) with two orifices (32) configured for attachment to the pleura, by suture, to avoid any risk of tension on the phrenic nerve (2).

7. A method of operation of the electrode as described claim 1, characterized in supplying the contactors (14, 15, 16, 17), taken two by two, sequentially, in four phases, each contactor in turn being anode or cathode.

8. A method of operation of the electrode as described claim 2, characterized in supplying the contactors (14, 15, 16, 17), taken two by two, sequentially, in four phases, each contactor in turn being anode or cathode.

9. A method of operation of the electrode as described claim 3, characterized in supplying the contactors (14, 15, 16, 17), taken two by two, sequentially, in four phases, each contactor in turn being anode or cathode.

10. A method of operation of the electrode as described claim 4, characterized in supplying the contactors (14, 15, 16, 17), taken two by two, sequentially, in four phases, each contactor in turn being anode or cathode.

11. A method of operation of the electrode as described claim 5, characterized in supplying the contactors (14, 15, 16, 17), taken two by two, sequentially, in four phases, each contactor in turn being anode or cathode.

12. A method of operation of the electrode as described claim 6, characterized in supplying the contactors (14, 15, 16, 17), taken two by two, sequentially, in four phases, each contactor in turn being anode or cathode.

* * * * *